United States Patent
Kent

(10) Patent No.: US 9,737,291 B2
(45) Date of Patent: Aug. 22, 2017

(54) LAPAROSCOPIC SURGICAL INSTRUMENT

(71) Applicant: Andrew Kent, Hindhead, Surrey (GB)

(72) Inventor: Andrew Stephen Harding Kent, Surrey (GB)

( * ) Notice: Subject to any disclaimer, the term of this patent is extended or adjusted under 35 U.S.C. 154(b) by 0 days.

(21) Appl. No.: 14/549,095

(22) Filed: Nov. 20, 2014

(65) Prior Publication Data
US 2015/0148822 A1    May 28, 2015

(51) Int. Cl.
*A61B 17/04* (2006.01)
*A61B 17/34* (2006.01)
*A61B 17/32* (2006.01)
*A61B 17/00* (2006.01)
*A61B 17/42* (2006.01)

(52) U.S. Cl.
CPC ........ *A61B 17/04* (2013.01); *A61B 17/00234* (2013.01); *A61B 17/0469* (2013.01); *A61B 17/32* (2013.01); *A61B 17/3417* (2013.01); *A61B 17/42* (2013.01); *A61B 2017/00424* (2013.01); *A61B 2017/00805* (2013.01); *A61B 2017/00991* (2013.01); *A61B 2017/0474* (2013.01); *A61B 2017/0496* (2013.01); *A61B 2017/320044* (2013.01); *A61B 2017/3456* (2013.01)

(58) Field of Classification Search
CPC .............. A61B 17/00234; A61B 17/04; A61B 17/0469; A61B 17/32; A61B 17/3417; A61B 17/42; A61B 2017/00424; A61B 2017/00805; A61B 2017/00991; A61B 2017/0474; A61B 2017/0496; A61B 2017/320044; A61B 2017/3456

USPC ........................................... 606/148
See application file for complete search history.

(56) References Cited

U.S. PATENT DOCUMENTS

| | | | | |
|---|---|---|---|---|
| 4,475,890 A | * | 10/1984 | Heidelbach | A61C 8/0018 433/173 |
| 4,493,315 A | * | 1/1985 | Iwahashi | A61H 7/001 601/135 |
| 4,509,516 A | * | 4/1985 | Richmond | A61B 17/32 606/144 |
| 5,112,344 A | * | 5/1992 | Petros | A61B 17/0469 128/DIG. 25 |
| 5,230,134 A | * | 7/1993 | Laue | B21D 53/88 29/428 |
| 6,929,625 B2 | * | 8/2005 | Bierman | A61M 25/02 128/DIG. 26 |
| 2006/0161041 A1 | * | 7/2006 | Forsell | A61F 2/0036 600/30 |
| 2009/0024156 A1 | * | 1/2009 | Chin | A61B 17/00008 606/194 |

(Continued)

FOREIGN PATENT DOCUMENTS

JP        2000139758 A  *  5/2000
WO    WO 2008002455 A2 *  1/2008 ............ A61F 11/006

*Primary Examiner* — Katherine M Shi
(74) *Attorney, Agent, or Firm* — Jennifer Meredith, Esq.; Meredith & Keyhani, PLLC

(57) ABSTRACT

The object of the present invention is to provide an improved laparoscopic, surgical instrument, particularly though not exclusively for gynaecology and in particular for Laparoscopic Colposuspension. According to the invention there is provided a laparoscopic, surgical instrument having an elongate shank, a ball head on one end and an eye in the other end. The instrument is such that the ball head is of a larger diameter than that of the elongate shank.

10 Claims, 1 Drawing Sheet

(56) References Cited

U.S. PATENT DOCUMENTS

2013/0283961 A1* 10/2013 Kaijala .................. G05G 1/506
74/512
2014/0289986 A1* 10/2014 Hani ....................... A61F 13/38
15/209.1

* cited by examiner

LAPAROSCOPIC SURGICAL INSTRUMENT

The present invention relates to a laparoscopic, surgical instrument.

Laparoscopic procedures, like all surgery, require great dexterity, with the added challenge that the steps in the operation cannot be seen directly, but have to be accessed through a telescope (laparoscope) and viewed on a screen. Most of this imaging is currently two dimensional with no perception of depth, but increasingly the trend is towards passive polarising three dimensional imaging.

In performing any surgical procedure the key is in attention to detail. The best techniques are simple and efficient. Minimal access surgical procedures are by definition limited in access and the numbers of ports (access points) that are available for instruments. As a consequence I have experienced a need for instruments that specifically adapted to the procedures and ideally multifunctional. I also find that the fewer instruments I have to hand the easier and quicker the procedures are to execute. In addition efficient surgery is important in reducing anaesthetic time. It also means that the procedures are executed more quickly with the ability to do more operations and therefore treat more patients in the available theatre time. In total this also reduces the cost of treatment.

I have devised a variation of a procedure called Laparoscopic Colposuspension. This is used to treat female urinary incontinence and anterior vaginal wall prolapse. This procedural technique requires tissue dissection between the bladder neck and vagina in the Cave of Retzius, and the placement of sutures between the upper anterior vaginal wall and the ilio-pectineal ligament.

The object of the present invention is to provide an improved laparoscopic, surgical instrument, particularly though not exclusively for gynaecology and in particular for my above variation.

According to the invention there is provided a laparoscopic, surgical instrument having:
  an elongate shank
  a ball head on one end
  an eye in the other end and in that the ball head is of a larger diameter than that of the elongate shank.

The instrument is preferably made from surgical grade stainless steel which provides a weight to the instrument allowing easy insertion via the laparoscopic ports. It can however be made from any rigid material that is suitable and safe for human use. It can be re-useable or disposable (single use).

It is in itself a dual function instrument. Firstly as a blunt dissector of tissues it allows me to access the area where I need to place stitches to allow me to do the operation. Inversion of the instrument allows me to tie hand thrown knots at the correct tension to elevate the anterior vaginal wall. This is done by the placement of the throws of sutures down a narrow access port (tube) into the abdomino-pelvic cavity. The dissecting part of the instrument doubles as a handle during this process.

Although this instrument has been specifically designed for this procedure it can be used in other keyhole operations that require the tying of knots to secure sutures place laparoscopically or tissue dissection.

In the nature of this procedure, the instruments used are longer than those required for conventional open incision surgery.

The elongate shank allows me to access the pelvis through a narrow port.

The ball head is preferably substantially spherical and preferably substantially 8 mm in diameter. It could nevertheless be between 4 mm and 15 mm in diameter, or between 6 mm and 13 mm, or between 6.5 mm and 10 mm, or between 5 mm and 8 mm and possibly even smaller or bigger. The constraints on it are that it should be of a larger diameter than that of the elongate shank, which itself cannot be reduced to a diameter appreciably less that 5 mm, without loss of rigidity. Equally the ball head cannot be appreciably larger in diameter without requiring an inconsistently large port.

The 8 mm ball head allows me to use a reduced diameter port or access tube, which requires a smaller incision with no requirement for deep dermal sutures. The ball head is however large enough to allow gentle blunt dissection (dissecting) with minimal tissue trauma. The end portion of the elongate shank comprising the eye maybe formed as a tongue. The tongue may range between 4 mm to 20 mm, 6 mm to 15 mm, 8 to 10 mm or 3 mm to 6 mm in length.

Even if not substantially spherical, the ball head is preferably continuously curved, possibly with inflexion close to the junction of the ball with the shank, whereby it has no step liable to snag on tissue or on the end of the port when being withdrawn from the body after dissection.

The eye in the other end of the instrument enables me to also use it for knot tying (knotter). Once a full-length (70-90 cm) stitch has been placed in the tissues, the instrument is inverted outside of the body. The standing part of the suture (with the needle attached) is passed through the eye of the instrument and the needle is secured and made safe with a standard surgical clip available on all surgical sets. The clip is then held by an assistant with a degree of tension on the standing part of the suture. The surgeon then ties the knot by making hand throws with the tail around the standing part. With an inward sliding action the throw is directed down the 8 mm port into the patient and placed at the correct location with the correct tension. The instrument is then withdrawn, still on the standing part, and the surgeon makes a second reverse throw to allow the formation of a square knot. This is then directed inwards with the instrument to lie against the first throw. The sequence is then repeated as many time as is required depending on the suture material used and tension required to create a secure surgical knot which will not come undone or loosen. The ball head provides a 'handle' and is gentle on the palm when tension is being applied.

The advantages of this technique is that it is a quick, simple way to tie and secure knots laparoscopically with any suture material of a suitable length. As the suture is passed through an intact eye in the end of the instrument it will not come off the standing part of the suture unless the suture breaks. This is especially important when the tip of the instrument is out of view in the port (where it passes through the abdominal wall). The knots can be tensioned and secured to the same strength as at open surgery. Indeed the instrument could be likened to a long finger placing each throw of the suture material in turn as one would when hand tying at open surgery.

To help understanding of the invention, a specific embodiment thereof together with a variant will now be described by way of example and with reference to the accompanying drawings, in which.

Figure 1:
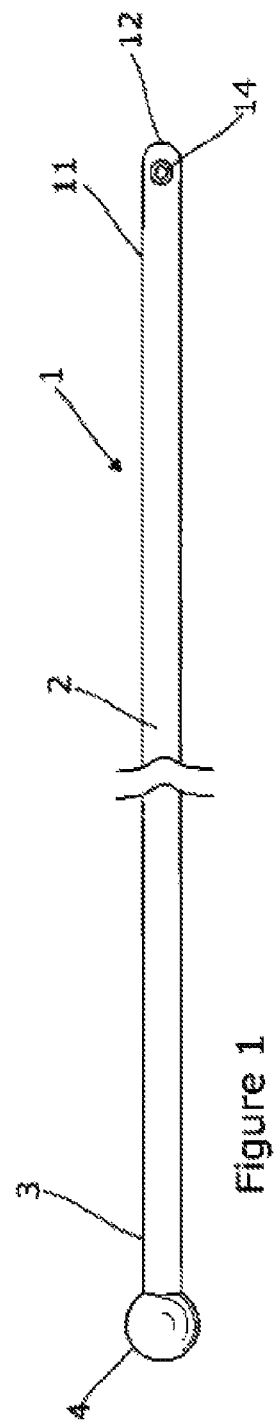
FIG. 1 is a side view of a laparoscopic, surgical instrument according to the invention.
Figure 2:
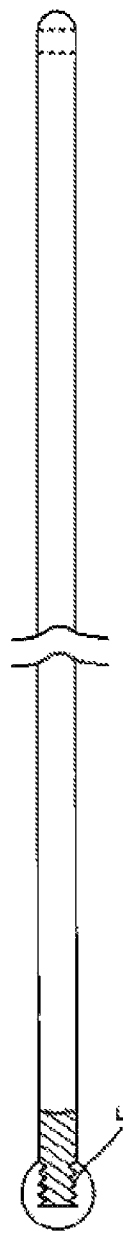
FIG. 2 is a partially sectioned plan view of the laparoscopic, surgical instrument of FIG. 1.

Referring to FIG. 1 of the drawing, a first a laparoscopic, surgical instrument 1 of the invention is of stainless steel has a 400 mm long shank 2 of 5 mm round rod. At one first end it has a threaded end 3 carrying an 8 mm spherical ball 4. The major diameter of the thread is that of the rod, whereby the joint between the ball and the thread is step-less or shouldered.

The other second end 11 of the rod is rounded 12 and has a 2 mm diameter eye 14, whose orifices are polished smooth to allow a suture to slide through the eye without chaffing or catching which would impede tying the knot and may damage the suture material causing it to break.

Figure 3:
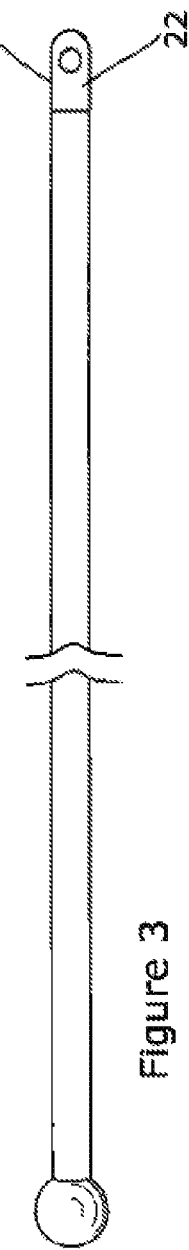
FIG. 3 is a view similar to FIG. 1 of a variant instrument.
Figure 4:
FIG. 4 is a view similar to FIG. 2 of the varied instrument.

Shown in FIG. 3 is a varied instrument, whose end portion 21 is ground away on both sides to leave a 2.5 mm tongue 22 through which the eye passes. Its orifices are again polished for smooth passage of the suture.

The invention is not intended to be restricted to the details of the above described embodiment. For instance the ball can have a plain bore and be soldered or welded onto the shank. Again it can be formed integrally with the shank by upsetting or forging. In any of these cases, it would be polished to provide smooth contours between the ball and the shank.

The invention claimed is:

1. A laparoscopic, surgical instrument having: a substantially straight, rigid elongate shank made of stainless steel having a first end with a ball head and a second integrally rounded end with an eye orifice therein;

wherein the ball head is of a larger diameter than that of the elongate shank, and wherein the end portion comprising the eye is formed as a tongue and the tongue has a length between 4 mm to 20 mm, 6 mm to 15 mm, 8 mm to 10 mm or 3 mm to 6 mm.

2. An instrument according to claim 1, wherein the ball head is substantially spherical.

3. An instrument according to claim 1, wherein the elongate shank is at least 5 mm in diameter.

4. An instrument according to claim 1, wherein the ball head is between 4 mm and 15 mm in diameter.

5. An instrument according to claim 1, wherein the ball head is between 6 mm and 13 mm in diameter.

6. An instrument according to claim 1, wherein the ball head is between 6.5 mm and 10 mm in diameter.

7. An instrument according to claim 1, wherein the ball head is between 5 mm and 8 mm in diameter.

8. An instrument according to claim 7, wherein the ball head is 8 mm in diameter.

9. An instrument according to claim 1, wherein the ball head is continuously curved.

10. An instrument according to claim 1, wherein the ball head comprises an inflexion close to the junction of the ball with the shank.

* * * * *